US008216171B2

(12) United States Patent
Kamen et al.

(10) Patent No.: US 8,216,171 B2
(45) Date of Patent: Jul. 10, 2012

(54) INDIVIDUAL DOSE PACKAGING

(75) Inventors: Dean Kamen, Bedford, NH (US); Larry B. Gray, Merrimack, NH (US); Matthew C. Harris, Bow, NH (US); Richard J. Lanigan, Concord, NH (US); Craig R. Steinfels, Manchester, NH (US); Brian D. Tracey, Litchfield, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 416 days.

(21) Appl. No.: 10/891,799

(22) Filed: Jul. 15, 2004

(65) Prior Publication Data

US 2005/0075596 A1  Apr. 7, 2005

Related U.S. Application Data

(60) Provisional application No. 60/488,306, filed on Jul. 18, 2003, provisional application No. 60/487,441, filed on Jul. 15, 2003.

(51) Int. Cl.
*A61M 35/00* (2006.01)
(52) U.S. Cl. .................................. 604/1; 604/3
(58) Field of Classification Search .................. 604/1–3, 604/11–18
See application file for complete search history.

(56) References Cited

U.S. PATENT DOCUMENTS

| 2,902,146 | A | * | 9/1959 | Doherty | 206/361 |
| 4,260,570 | A | * | 4/1981 | Ravel | 264/46.6 |
| 4,902,275 | A | | 2/1990 | Fassbind | 604/1 |
| 4,952,204 | A | * | 8/1990 | Korteweg | 604/1 |
| 5,572,997 | A | * | 11/1996 | Kanner et al. | 600/369 |
| 5,713,874 | A | * | 2/1998 | Ferber | 604/198 |
| 5,874,045 | A | * | 2/1999 | Chisum | 422/58 |
| 6,080,783 | A | | 6/2000 | Davidson et al. | 514/494 |
| 6,365,624 | B1 | | 4/2002 | Davidson et al. | 514/494 |
| 6,406,451 | B1 | | 6/2002 | Rowe | 604/1 |
| 6,516,947 | B1 | * | 2/2003 | Van Dyke et al. | 206/361 |
| 6,902,538 | B2 | * | 6/2005 | Bennett | 604/1 |
| 2003/0233063 | A1 | * | 12/2003 | Nakatani | 604/2 |

OTHER PUBLICATIONS

Jack Aurora, PhD, Development of Nasal Delivery Systems: A Review; Drug Delivery Technology, vol. 2, No. 7, Oct. 2002.

* cited by examiner

*Primary Examiner* — Lynne Anderson
(74) *Attorney, Agent, or Firm* — Michelle Saquet Temple

(57) ABSTRACT

A method for packaging an agent for delivery within a body cavity. A reservoir within a package contains a specified quantity of the agent and is either contiguous with, or coupled to, a dispensing node such as a swab. Depth of insertion of the dispensing node into the body cavity is restricted to a specified depth by a penetration-restricting feature that forms part of the package.

8 Claims, 7 Drawing Sheets

INDIVIDUAL DOSE PACKAGING

CROSS REFERENCE TO RELATED APPLICATIONS

This application claims priority from U.S. Provisional Application No. 60/487,441, filed Jul. 15, 2003, and from U.S. Provisional Application No. 60/488,306, filed Jul. 18, 2003. The disclosures of both provisional applications are incorporated herein, in their entireties, by reference.

TECHNICAL FIELD

The present invention relates to the field of delivery of agents into cavities of the human body, and, more particularly, to nasal delivery of pharmaceutical, therapeutic, nutritional, cosmetic or homeopathic agents.

BACKGROUND OF THE INVENTION

The rich vasculature of the nasal mucosa provides a desirable avenue for the introduction of various agents. In particular, the highly vascularized lateral wall of the bulbous portion of the nasal cavity provides a particularly efficient route for absorption or adsorption of such agents.

It is known that absorption or adsorption of a material increases with residence time between the material and epithelial tissue in the nose, or other body cavity. On the other hand, the activity of cilia acts to clear the mucous tissue of dust or other particles trapped in mucous tissue.

Methods for delivery of agents to the nasal membranes include delivery in the form of drops, sprays, powders, or gels. It is also known that increasing the viscosity of a solution of therapeutic agent may have the effect of retaining the agent in the face of cilial action, thereby prolonging the therapeutic effect of the agent, and, thus, gels have come to be used for delivering such agents. Examples of gel-borne agents for nasal delivery are provided in U.S. Pat. Nos. 6,080,783 and 6,365,624, to Davidson et al., which are incorporated herein by reference.

One problem that presents itself, however, is that of optimizing the residence time in a region of particular efficacy, and, at the same time, providing a convenient application modality for the user that is neither messy nor difficult to use.

SUMMARY OF THE INVENTION

In a first embodiment of the invention there is provided a method for packaging an agent, such as but not limited to a therapeutic, pharmaceutical, nutritional, cosmetic or homeopathic agent, for delivery within a body cavity. The method has steps of:
  a. coupling a reservoir, disposed within a package and containing a specified quantity of the agent, to a dispensing node, the package having a penetration-restricting feature; and
  b. coupling the dispensing node to the package in such a manner as to limit a depth of insertion of the dispensing node into the body cavity to a specified depth.

In accordance with further embodiments of the invention, the package limits the depth of insertion by providing the user with a tactile guide indicating optimal insertion depth. In accordance with further embodiments of the invention, the dispensing node may be a swab, and, moreover, the reservoir and the swab may be identical. The swab may be covered with a sheath impermeable to the agent that is capable of retraction so as to expose the dispensing node for insertion into the body cavity while allowing handling of the package without touching the therapeutic agent.

In accordance with yet another embodiment of the invention, a pair of reservoirs containing the agent may be provided, with each of the pair of reservoirs coupled to a separate dispensing node, where the two dispensing nodes are separated in such a manner that the dispensing nodes may be inserted simultaneously, one into each nostril of the nose of the subject.

In accordance with yet further embodiments of the invention, an agent delivery product is provided for delivering the agent within a body cavity. The product has a swab coated with the agent and coupled to a shaft having a length and packaging impermeable to the agent for encasing the swab, the packaging characterized by a penetration-restricting feature disposed in such a manner as to restrict a depth of insertion of the swab into the body cavity to a depth determined by the penetration-restricting feature and the length of the shaft.

In accordance with yet further embodiments of the invention, a method is provided for manufacture of an agent delivery product. The method of manufacture includes steps of:
  a. forming depressions in a base sheet;
  b. dispensing a gel containing the agent in the depressions in the base sheet;
  c. sealing a cover sheet to the base sheet to form a sealed package; and
  d. cutting the sealed package into a specified shape.

In accordance with other embodiments of the invention, a dispensing node is placed on the base sheet, the dispensing node being coated with an agent either before or after placement on the base sheet. Alternatively, the dispensing node may be placed in one depression on the base sheet and the agent may be placed in another depression on the base sheet for later application.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

The term "agent" as used herein refers to a substance or substances that are introduced into the body cavity, particularly, the nasal cavity. Furthermore, the agent may be a pharmaceutical, therapeutic, homeopathic, nutritional or cosmetic agent.

Figure 1A:
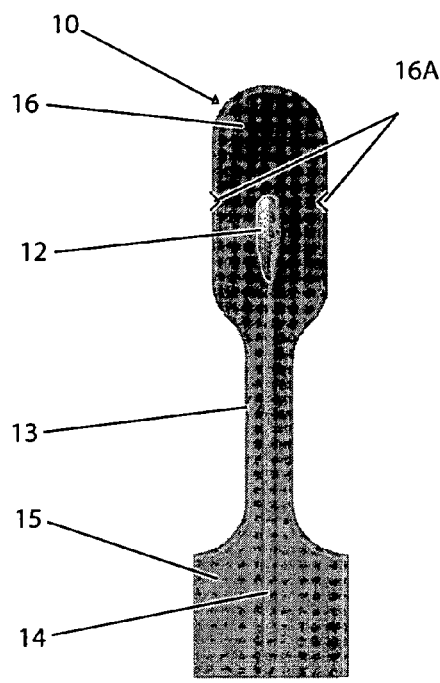
FIGS. 1A and 1B illustrate components of a package for an applicator swab in accordance with embodiments of the present invention, as sealed and as opened, respectively.
Figure 1B:
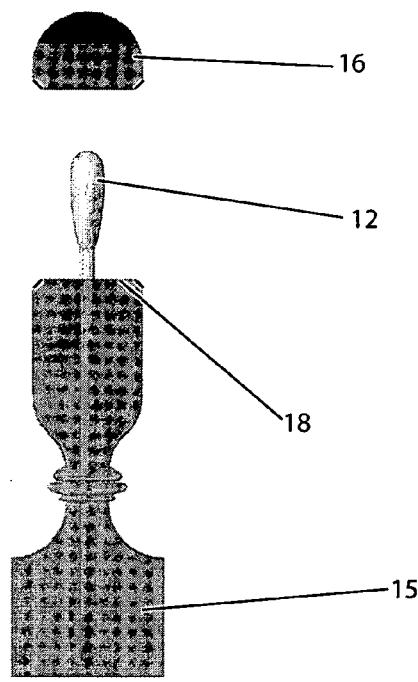

Referring first to FIGS. 1A and 1B, a preferred embodiment of the present invention is shown, in which a dispensing node 12 is disposed within a consumer point-of-sale package or agent delivery product designated generally by the numeral 10. Dispensing node 12 may be, as in the embodiment shown, a swab, such as a cotton pledget, coated with a gel that contains an agent for introduction into a body cavity. Dispensing node 12 need not be a swab, however, and other embodiments of the invention with ducts are described below, for example, in reference to FIGS. 3A, 3C and 3D.

In the present description, the body cavity to which reference is made is typically the nose, however it is to be understood that the use of the methods and materials described herein in the context of other body cavities is within the scope of the present invention. Moreover, while the present description refers to the agent as contained within a gel, it is to be noted that liquids or powders may be handled in analogous ways, within the scope of the present invention as described herein and as claimed in any appended claims.

Package 10 is typically fabricated by joining flexible films made of any of a variety of materials, such as plastic and foils, and, as a more particular example, sheets of urethane. The package may be formed by heat-welding, or otherwise joining, materials that are substantially impermeable to the gel so as to prolong the shelf-life of the product. Swab 12 may be coupled to a shaft 14 which allows the swab to protrude from package 10 when tab 16 is removed from the package by the user in order to expose the swab. Tab 16 is typically removed by tearing along a stress concentrate in the packaging material, such as a notch or a slit.

The user may expose the swab by a variety of methods. Preferably, the user tears across the top of the packaging material to expose the swab. Alternatively, the user may tear along the center of the packaging material, that is, down from the top of the swab and towards the opposite end of the swab, to expose the swab. Furthermore, the user may tear the packaging material by grasping each half of the packaging material and pulling it apart, to expose the swab.

Figure 1C:
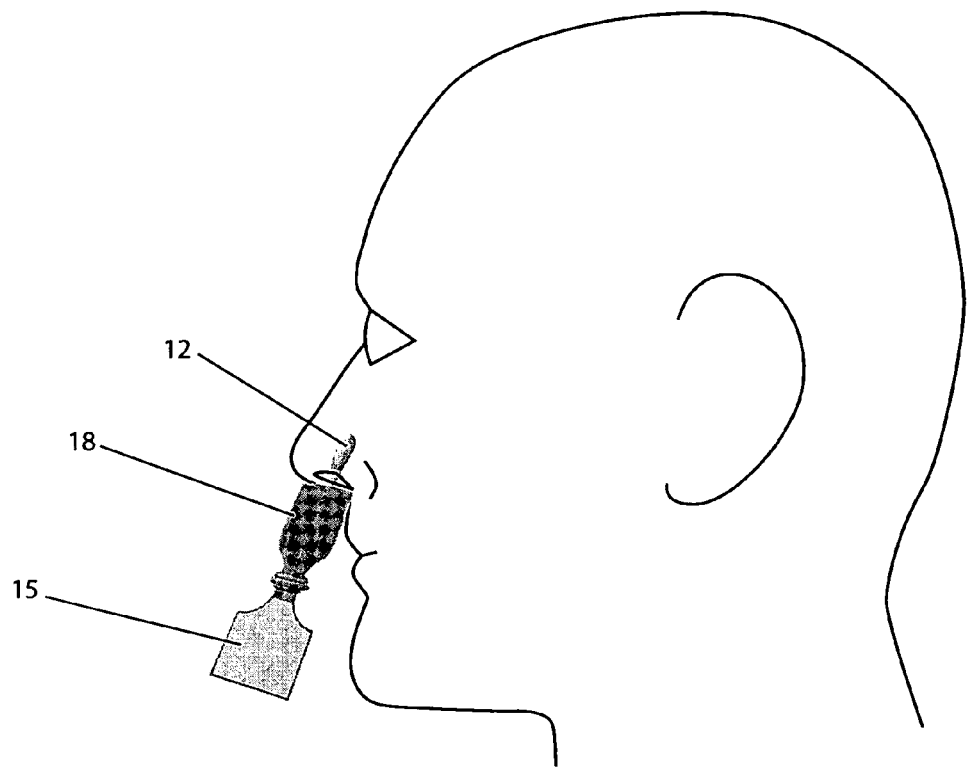
FIG. 1C illustrates the penetration-restricting feature of the packaging to restrict the depth of insertion of the dispensing node into the body cavity.

FIG. 1B shows the applicator package 10 of FIG. 1A after opening by the user. A collapsible sheath 18 may then be retracted, as shown in FIGS. 1B and 1C, in order to expose swab 12 to allow the swab to be inserted into the nose or other body cavity. The user holds finger tab 15, advantageously allowing the gel coating of the swab to be dispensed while minimizing the exposure of the user's hands to the gel. Preferably, the user's hands are not exposed to the gel. An additional advantage of the embodiment depicted in FIG. 1C is that the collapsible sheath may provide tactile feedback to the user with respect to depth of insertion of the swab. Thus, the user may know when the swab is inserted sufficiently deeply for desired delivery of the gel by virtue of the sheath touching the edge of the nostril as shown in FIG. 1C. The length of shaft 14 is tailored to a desired depth of penetration relative to the end of the retracted sheath. Sheath 18 is withdrawn, on opening, from flexible neck 13 of the applicator package.

Following retraction of the sheath 18, additional gel may be retained within the sheath 18 as the sheath 18 acts as a reservoir for the gel. The sheath 18 may be subsequently extended, resulting in a further application of gel to the swab 12. Upon a further retraction of the sheath 18, gel may be applied to the same or to a different nostril.

Figure 1D:
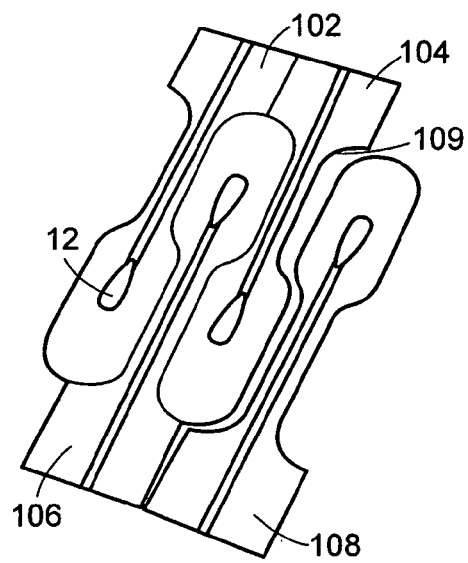
FIGS. 1D, 1E, and 1F depict sterile packaging of an applicator swab in embodiments providing for minimal packaging waste.
Figure 1E:
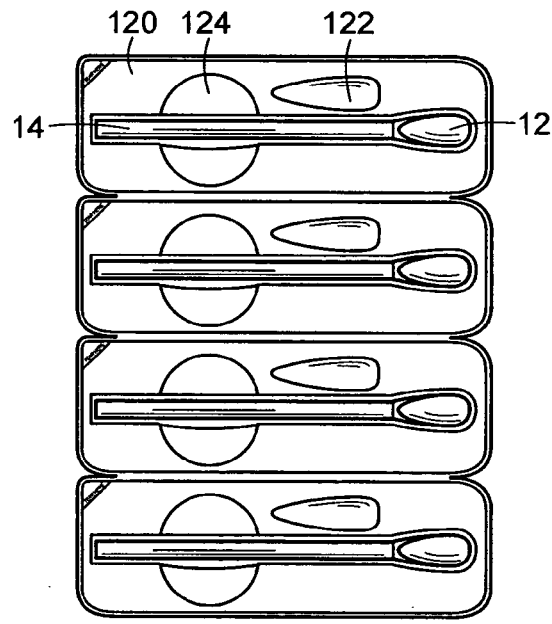
Figure 1F:
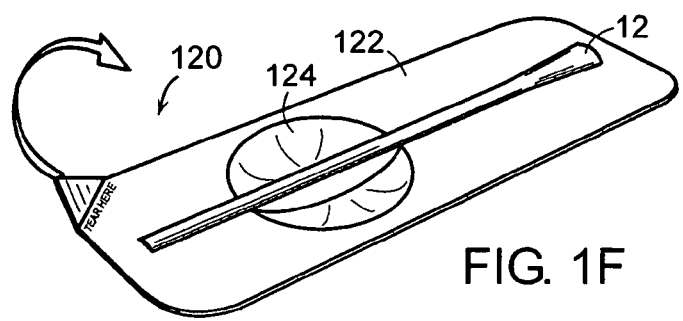

An advantageous feature of the present invention is the amenability of various of the embodiments described herein to minimal-waste packaging. For example, referring now to the embodiment depicted in FIG. 1D, with the package cover removed, applicator swab 12 is individually packaged within sterile package 102, in continuous conjunction with sterile packages 104, 106, and 108. Sterile package 108 is depicted being detached along perforation line 109 from adjoining package 104 and 106. An alternate packaging scheme is shown in FIG. 1E. Additional depressions 122 and 124 may be provided, by vacuum forming or otherwise, in the base sheet of package 120 as a supplemental reservoir of gel containing the agent, or to facilitate removal of shaft 14 by the user. As shown in FIG. 1E, depression 122 may be a reservoir of gel and depression 124 may facilitate the removal of the shaft 14 by the user. FIG. 1F is a perspective view of package 120 further clarifying depressions 122 and 124 described above.

Figure 2:
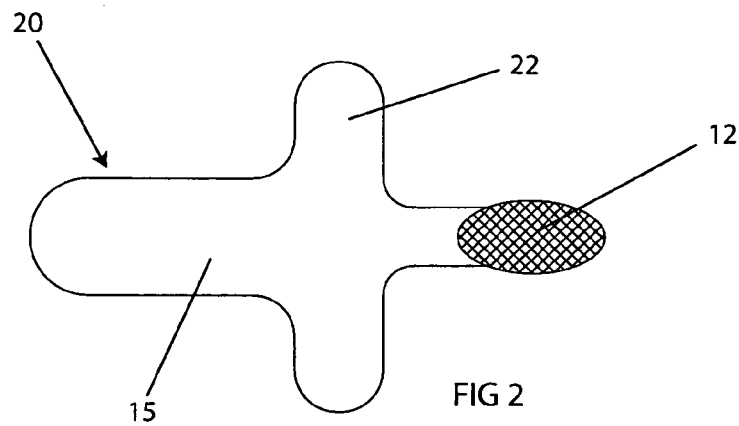
FIG. 2 is a top view of a swab applicator package in accordance with an embodiment of the present invention.

Referring now to FIG. 2, package or agent delivery product 20, shown here after opening, such that coated swab 12 is exposed, may be shaped such as to form features such as wings 22, thereby limiting, by virtue of their lateral extent, the depth to which swab 12 may be inserted into the user's nostril. The base portion of package 20 comprising finger tab 15 is preferably flat for ease of gripping by the user.

Figure 3A:
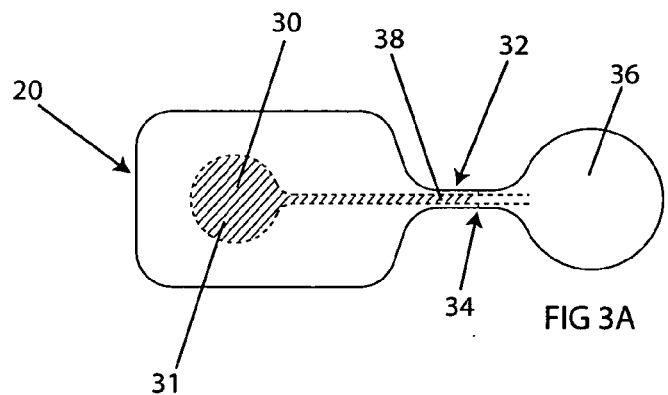
FIG. 3A is a cross section of an applicator package in accordance with a further embodiment of the present invention.
Figure 3B:
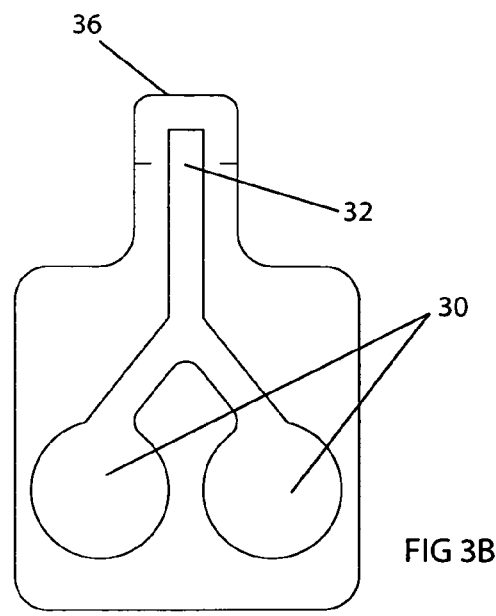
FIG. 3B is a cross section of an applicator package containing a separate gel reservoir for each nostril, in accordance with a further embodiment of the present invention.

In accordance with another embodiment of the invention depicted in FIG. 3A, gel 31 containing the agent may be provided within a sealed reservoir 30 within the applicator package 20. Reservoir 30 is coupled to a dispensing node 32 via duct 38, here made accessible by the user by removing a frangible seal 34, in this case, by tearing away tab 36. In other embodiments of the invention, multiple reservoirs 30 may be provided. FIG. 3B shows two reservoirs 30, each coupled to a single dispensing node 32. In this case, the user tears off tab 36, inserts dispensing node 32 and, by pressing on the outside of the package, squeezes the contents of each reservoir 30 into a separate nostril.

Figure 3C:
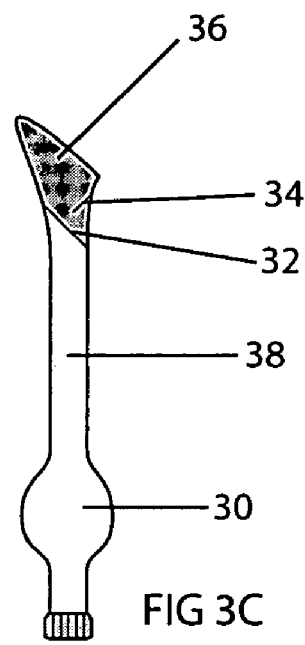
FIGS. 3C and 3D illustrate inner and outer views of a package containing a soft extruded tube applicator in accordance with embodiments of the present invention.
Figure 3D:
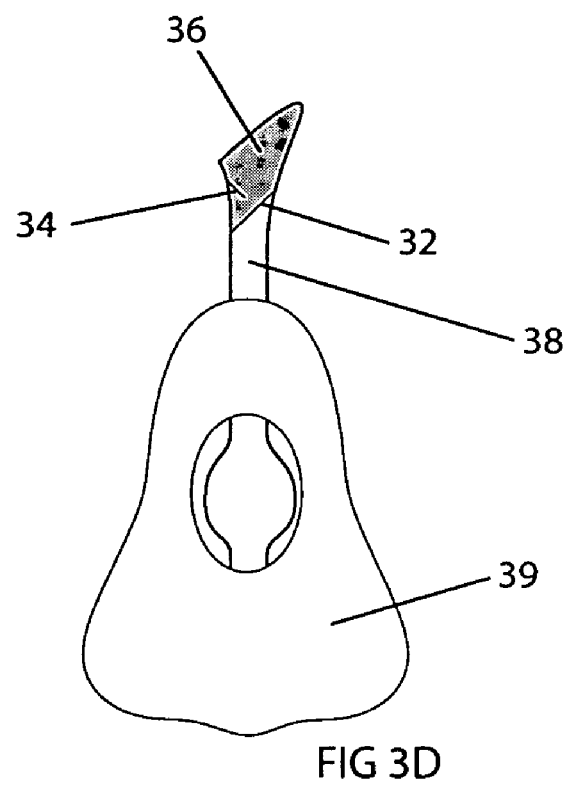

Referring now to FIG. 3C, showing an embodiment of the invention without a swab, dispensing node 32 is initially provided to the consumer with a heat sealed covering 36, referred to above as a 'tab'. Covering 36 is torn away at frangible seal 34 to expose the dispensing node. Dispensing node 32 is coupled to gel-containing reservoir 30 by means of a duct 38, which, in the embodiment shown, is soft extruded tubing that may be used, in the manner of a swab, to deposit the gel at a preferred depth in a body cavity. Duct 38 may advantageously be formed using the substance to be contained within reservoir 30 for purposes of manufacturing the duct 38. The duct 38 may be extruded simultaneously into the tube during the manufacturing process. Furthermore, the gel may be inserted into the tube during the extrusion process. Moreover, the enclosing package 39, shown in FIG. 3D and also referred to as a 'tab', may serve the function, described above, of defining, by virtue of the tactile features of its width, the depth to which dispensing node 32 is optimally inserted into the nose.

Figure 4A:
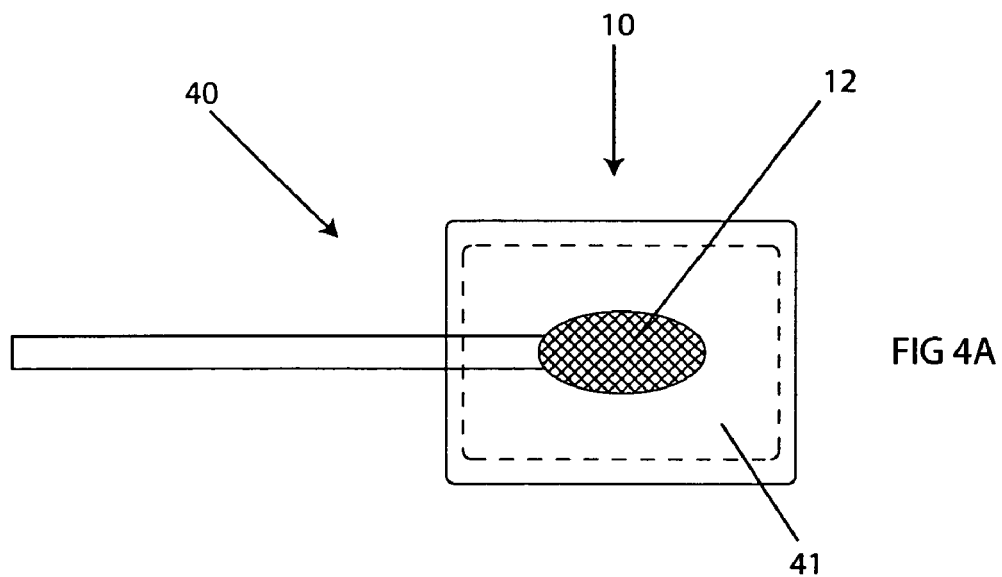
FIGS. 4A and 4B illustrate cross sections of two further embodiments of applicator swab packages as described in the present invention.
Figure 4B:
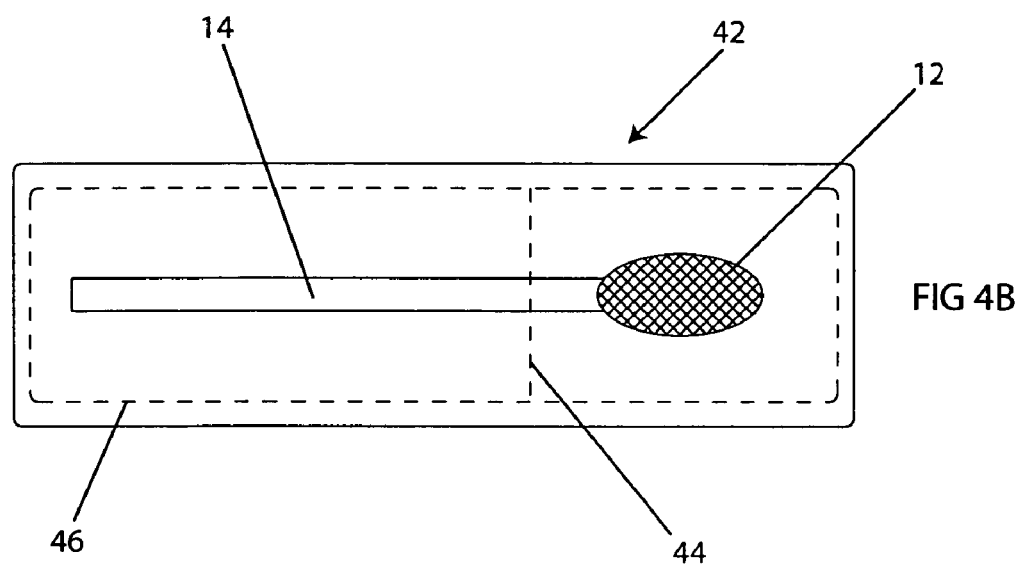

Various embodiments of the invention provide, either that swab 12 is enclosed within heat-sealed sheeting 41 to form package 40 (FIG. 4A), or, alternatively, in addition to primary seal 44, a secondary seal 46 is provided that encompasses shaft 14 to form package 42 as shown in FIG. 4B.

Figure 5:
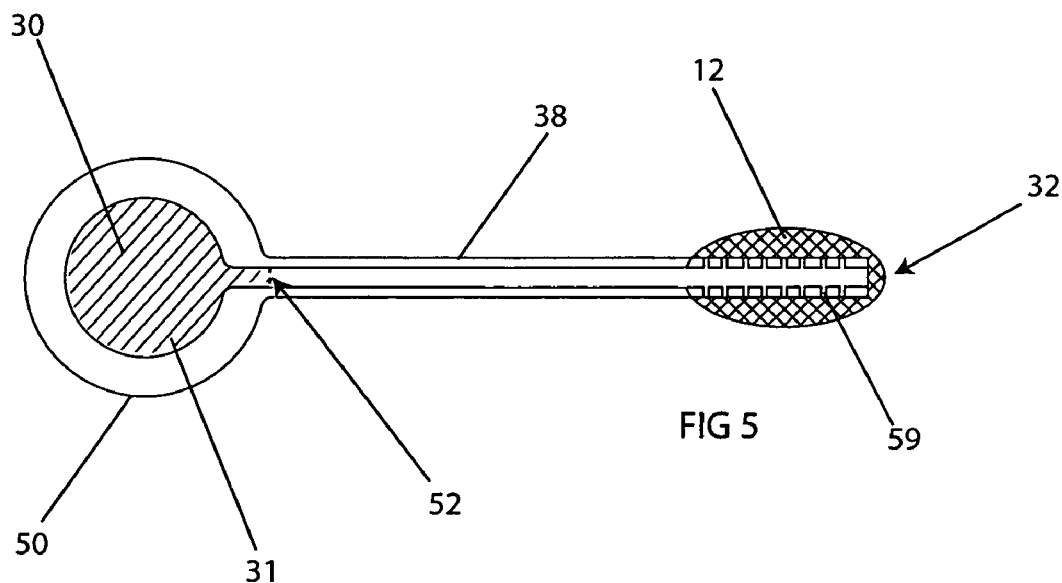
FIG. 5 is a cross section of a swab applicator package in accordance with yet a further embodiment of the present invention.
Figure 6:
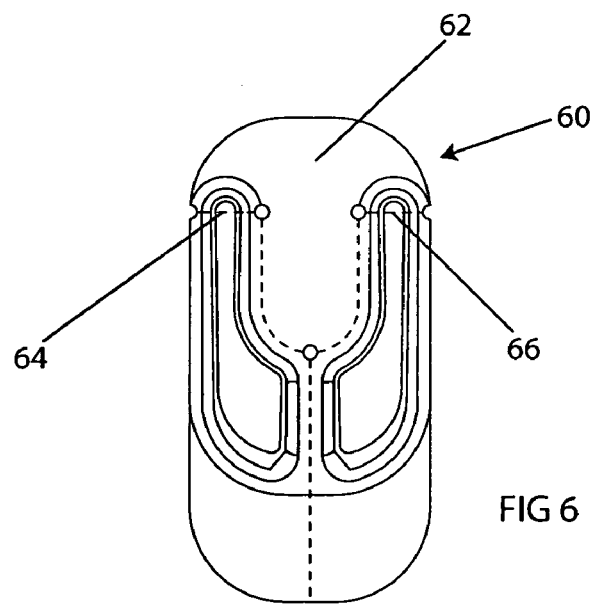
FIG. 6 is a cross section of an applicator package with two detachable sections with each section containing an embodiment of the present invention with a dispensing node.
Figure 7:
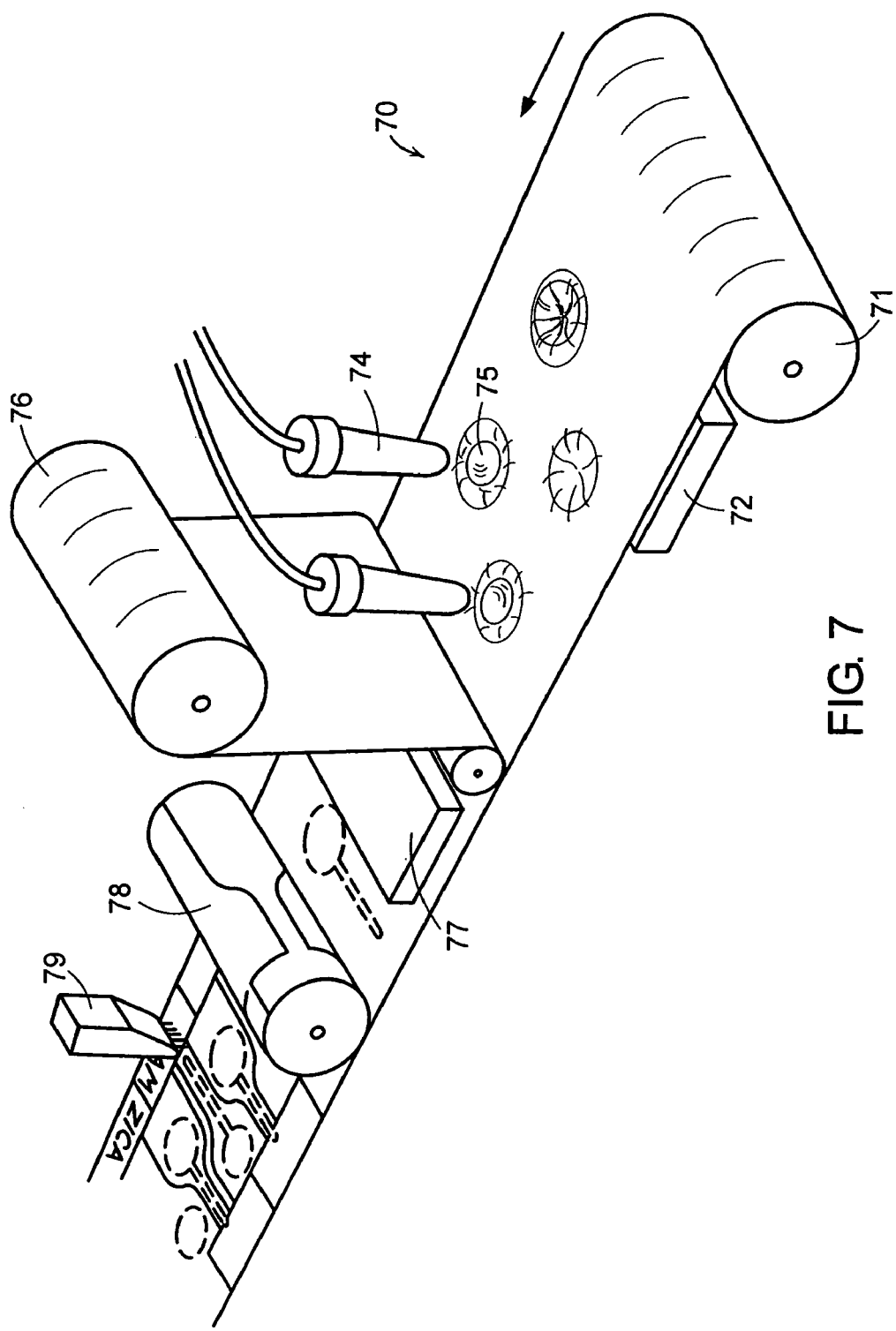
FIG. 7 is a perspective view showing an assembly process for manufacturing swab applicator packages in accordance with an embodiment of the present invention.

Referring now to FIG. 5, gel reservoir 30 within heat-welded flexible film enclosure 50 may be coupled to a dispensing node 32 in swab 12 by a duct 38 where fluid communication between the gel reservoir 30 and the dispensing node 32 require only open rupture by the user of frangible seal 52. As shown in FIG. 5, preferably, there may be side fenestrations 59 in the part of the duct 38 within the swab 12 to allow the gel 31 to directly penetrate into the swab 12. Additionally, in other embodiments, the duct 38 may dispense its contents directly into the swab 12 or the body cavity. Other embodiments of agent delivery products showing the packaging of parallel applicators 62 are illustrated in FIG. 6, in this embodiment, as two sections. When tear-away tab 62 is removed, two dispensing nodes 64 and 66 are exposed that may be applied simultaneously, one to each nostril of the user.

Disposable applicators or agent delivery products, of the sort discussed in the foregoing description, may advantageously be manufactured in accordance with a method now described with reference to FIG. 7. A base sheet 70 of film such as urethane, or other suitable material, is drawn from base sheet roll 71. Vacuum former 72 draws reservoirs 73 into sheet 70. Other methods, such as matched die forming, may be used for form reservoirs 73 into sheet 70. Reservoirs 73 are filled by dispensers 74 with prescribed quantities of gel 75. A cover sheet of urethane is drawn from cover sheet roll 76 to cover the base sheet and heat-welded to the base sheet by heat sealer 77. Unit packages are cut to shape by die cutter 78 and printing is applied to the completed packages by printer 79.

In view of the foregoing, it will therefore be understood that the scope of the invention as defined in the following claims is not limited to the embodiments described herein, and that the above and numerous additional variations and modifications could be made thereto without departing from the scope of the invention as defined in the following claims.

What is claimed is:

1. A method for packaging an agent for delivery within a body cavity, the method comprising:

a. coupling a reservoir disposed within a package and containing a specified quantity of the agent to a dispensing node, the package comprising:
   a flexible neck having two ends;
   a removable tab connected to one of the two ends of the flexible neck; and
   a finger tab connected to the other of the two ends of the flexible neck,
   wherein the flexible neck providing a penetration-restricting feature,
   wherein the penetration-restricting feature is capable of retraction onto itself, and
   wherein the flexible neck comprising a width that is less than the width of the finger tab and the removable tab; and
b. coupling the dispensing node to the package wherein the package restricts a depth of insertion of the dispensing node into the body cavity to a specified depth.

2. A method for packaging in accordance with claim 1, wherein restriction of a depth of insertion is at least on the basis of tactile feedback.

3. A method for packaging in accordance with claim 1, wherein the dispensing node includes a swab.

4. A method for packaging in accordance with claim 3, wherein the reservoir and the swab are identical.

5. A method for packaging an agent for delivery within a body cavity, the method comprising:

a. coating a swab with the agent; and
b. attaching the swab to a package comprising:
   a flexible neck having two ends;
   a removable tab connected to one of the two ends of the flexible neck; and
   a finger tab connected to the other of the two ends of the flexible neck,
   wherein the flexible neck comprising a width that is less than the width of the finger tab and the removable tab, the flexible neck providing a penetration-restricting feature in such a manner as to restrict a depth of insertion of the swab into the body cavity to a depth determined by the penetration-restricting feature,
   wherein the penetration-restricting feature is capable of retraction onto itself.

6. A method for optimizing the residence time of an agent at a site of delivery within a body cavity, the agent coating a swab, the method comprising:

coupling the swab to a shaft characterized by a length;
encasing the shaft in a package wherein the package comprising:
   a flexible neck having two ends;
   a removable tab connected to one of the two ends of the flexible neck; and
   a finger tab connected to the other of the two ends of the flexible neck,
   wherein the flexible neck comprising a width that is less than the width of the finger tab and the removable tab,
   wherein the flexible neck providing a penetration-restricting feature,
   wherein the shaft is fully encased in the package, and
   wherein the package is substantially impermeable to the agent; and
inserting the swab into the body cavity to a depth determined by the penetration-restricting feature and the length of the shaft.

7. A method for packaging a agent for delivery within a body cavity, the method comprising:

a. coating a swab with the agent;
b. embedding the swab within a sterile package; and
c. covering the swab with a sheath impermeable to the agent, wherein the sheath comprising:
   a flexible neck having two ends;
   a removable tab connected to one of the two ends of the flexible neck; and
   a finger tab connected to the other of the two ends of the flexible neck, wherein the flexible neck comprising a width that is less than the width of the finger tab and the removable tab, and
   wherein the flexible neck is capable of retraction onto itself thereby providing a penetration-restricting feature.

8. The method of claim 7, further comprising extending the sheath and retracting the sheath to expose the swab, such that the agent in a reservoir may be further applied to the swab.

* * * * *